US009296676B2

(12) United States Patent
Devaux et al.

(10) Patent No.: US 9,296,676 B2
(45) Date of Patent: Mar. 29, 2016

(54) PROCESS FOR MANUFACTURING ACROLEIN/ACRYLIC ACID

(75) Inventors: Jean-Francois Devaux, Soucieu en Jarrest (FR); Jean-Luc Dubois, Millery (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 13/981,927

(22) PCT Filed: Jan. 26, 2012

(86) PCT No.: PCT/IB2012/000396
§ 371 (c)(1),
(2), (4) Date: Aug. 20, 2013

(87) PCT Pub. No.: WO2012/101526
PCT Pub. Date: Aug. 2, 2012

(65) Prior Publication Data
US 2013/0324758 A1    Dec. 5, 2013

(51) Int. Cl.
| | |
|---|---|
| *C07C 51/16* | (2006.01) |
| *C07C 319/02* | (2006.01) |
| *C07C 45/28* | (2006.01) |
| *C07C 253/18* | (2006.01) |
| *B01J 27/19* | (2006.01) |
| *B01J 27/199* | (2006.01) |
| *C07C 253/26* | (2006.01) |
| *C07C 319/18* | (2006.01) |
| *C07C 45/35* | (2006.01) |
| *C07C 45/52* | (2006.01) |
| *C07C 45/65* | (2006.01) |
| *C07C 51/235* | (2006.01) |

(52) U.S. Cl.
CPC ............... *C07C 51/16* (2013.01); *B01J 27/19* (2013.01); *B01J 27/199* (2013.01); *C07C 45/28* (2013.01); *C07C 45/35* (2013.01); *C07C 45/52* (2013.01); *C07C 45/65* (2013.01); *C07C 51/235* (2013.01); *C07C 253/18* (2013.01); *C07C 253/26* (2013.01); *C07C 319/02* (2013.01); *C07C 319/18* (2013.01); *B01J 2523/00* (2013.01)

(58) Field of Classification Search
CPC ........ C07C 47/22; C07C 57/04; C07C 47/02; C07C 255/08; B01J 2523/68; B01J 23/8885; B01J 27/19
See application file for complete search history.

(56) References Cited

U.S. PATENT DOCUMENTS

| | | | |
|---|---|---|---|
| 4,381,411 | A | 4/1983 | Pedersen et al. |
| 5,387,720 | A | 2/1995 | Neher et al. |
| 2008/0214880 | A1* | 9/2008 | Dubois et al. .................. 585/500 |
| 2010/0204502 | A1* | 8/2010 | Dubois .......................... 558/315 |
| 2011/0257355 | A1* | 10/2011 | Moriguchi et al. ........ 526/317.1 |

FOREIGN PATENT DOCUMENTS

| | | |
|---|---|---|
| EP | 2 039 674 A2 | 3/2009 |
| FR | 695.931 | 12/1930 |
| JP | 54046705 A2 | 4/1979 |
| JP | 10218831 A2 | 8/1998 |
| WO | WO 2006/087084 A2 | 8/2006 |
| WO | WO 2006/087084 A3 | 8/2006 |
| WO | WO 2009/044081 A1 | 4/2009 |
| WO | WO 2009/127889 A1 | 10/2009 |
| WO | WO 2009/128555 A2 | 10/2009 |
| WO | WO 2010/046227 A1 | 4/2010 |
| WO | WO 2010/074177 A1 | 7/2010 |

OTHER PUBLICATIONS

Zhang et al. "Reaction pathways for selective oxidation of propane to acrolein over Ce—Ag—Mo—P—O catalysts" Applied Catalysis A: General 2009, 353, 24-31.*
Min et al. "Remarkable Effect of Iron-Substitution for Molybdenum in Phosphododecamolybdate on Oxidative Dehydrogenation of 2-Propanol" Chem. Lett. 2001, 30, 28-29.*
Hargis et al, Oxidation of some Organic anic Compounds by an Oxide of Arsenic, Antimony, or Bismuth.—I&E Product Research and Development, vol. 5, No. 1, Mar. 1966 pp. 72-75.
Ai, M., Design of Selective Catalysts for Oxidative Dehydrogenation—Kinetics and Catalysis, vol. 44, No. 2 (2003) pp. 198-201.
Hu et al, The Effect of Cation Type and H+ on the Catalytic Activity of the Keggin Anion [PMo12O40]3-—in the Oxidative Dehydrogenation of Isobutyraldehyd—Journal of Catalysis 195, (2000) pp. 360-375.
Cicmanec, et al Kintics of Oxidative Dehydrogenation of Isobutyraldehyde Over Cs2HPMo12O40 Catalyst—React. Kinet. Catal. Lett. vol. 81, (2004) pp. 383-391.
Soares et al, Methanol Selective Oxidation to Formaldehyde over Iron-Molybdate Catalysts—Catalysis Review, 47 (2004) pp. 125-174.

* cited by examiner

*Primary Examiner* — Nyeemah A. Grazier
*Assistant Examiner* — Amanda L Aguirre
(74) *Attorney, Agent, or Firm* — Lynn B. Morreale

(57) ABSTRACT

The present invention relates to the selective elimination of propanal in acrolein-rich streams to produce acrolein and/or acrylic acid and/or acrylonitrile and/or methylmercaptopropionaldehyde containing low amount of propanal and/or propionic acid and/or propionitrile. One subject of the present invention is a process for manufacturing acrolein comprising a step of selective elimination of propanal in an acrolein-rich stream in contact with a catalyst comprising at least molybdenum. Another subject of the present invention is a process for manufacturing acrylic acid from glycerol including a step of selective elimination of propanal in an acrolein-rich stream in contact with a catalyst comprising at least molybdenum.

13 Claims, No Drawings

PROCESS FOR MANUFACTURING ACROLEIN/ACRYLIC ACID

CROSS-REFERENCE TO RELATED APPLICATIONS

This application is a national stage application under 35 U.S.C. §371 of PCT/IB2012/000396, filed Jan. 26, 2012, which claims benefit to PCT/IB2011/000468, filed on Jan. 28, 2011, all of which are hereby incorporated by reference herein in their entireties.

The work leading to this invention has received funding from the European Community's Seventh Framework Program FP7/2007-2013 under grant agreement n° 228867.

TECHNICAL FIELD

The present invention relates to the selective elimination of propanal in acrolein-rich streams to produce acrolein and/or acrylic acid and/or acrylonitrile containing low amount of propanal and/or propionic acid and/or propionitrile.

One subject of the present invention is a process for manufacturing acrolein comprising a step of selective elimination of propanal in an acrolein-rich stream. Another subject of the present invention is a process for manufacturing acrylic acid from glycerol including a step of selective elimination of propanal in an acrolein-rich stream.

BACKGROUND ART

Acrolein is a key intermediate for the synthesis of methylmercaptopropionaldehyde and of methionine, a synthetic aminoacid used as an animal feed supplement, which has emerged as a substitute for fishmeal. Acrolein is also a non-isolated synthetic intermediate of acrylic acid and acrylonitrile for which the importance of their applications and its derivatives is known. Acrolein also leads, via reaction with methyl vinyl ether then hydrolysis, to glutaraldehyde, which has many uses in leather tanning, as a biocide in oil well drilling and during the treatment of cutting oils, and as a chemical sterilant and disinfectant for hospital equipment. Acrolein also leads to pyridine or glutaraldehyde.

Acrylic acid is a compound that is used essentially as polymerization monomer or comonomer for the manufacture of a very broad range of final products. These final products are manufactured by polymerization of the acid or of the derivatives of this acid, in the ester (polyacrylates) or amide (polyacrylamides) form. A very important outlet for acrylic acid is the manufacture of superabsorbents, in which a partially neutralized (mixture of acrylic acid and sodium acrylate or acrylates of other cations) acrylic acid is polymerized, or else acrylic acid is polymerized and the polyacrylic compound obtained is partially neutralized. These polymers are used as is or as copolymers in fields as varied as hygiene, detergents, paints, varnishes, adhesives, paper, textiles, leather, and the like.

Acrolein and/or acrylic acid are produced industrially by oxidation of propylene using oxygen or an oxygen-comprising mixture in the presence of catalyst systems based on mixed oxides. This reaction is generally carried out in the gas phase and generally in two stages to give acrylic acid: the first stage carries out the substantially quantitative oxidation of the propylene to give an acrolein-rich mixture, in which acrylic acid is a minor component, and then the second stage carries out the selective oxidation of the acrolein to give acrylic acid.

The reaction conditions of these two stages, carried out in two multitubular reactors in series or in a single reactor comprising the two reaction stages in series, are different and require catalysts suited to the reaction; however, it is not necessary to isolate the acrolein from the first stage during this two-stage process.

The starting materials used for acrolein or acrylic acid production result from oil or natural gas and consequently the acrolein or acrylic acid are formed from a non-renewable fossil carbon starting material. In the context of the commitments of the majority of industrialized countries to reduce emissions of greenhouse gases, it appears particularly important to manufacture novel products based on a renewable starting material, contributing to reducing the environmental effects and global warming potential.

Glycerol is derived from plant oils in the production of biodiesel fuels or oleochemicals such as fatty acids or fatty alcohol or fatty esters. Glycerol is one of the raw materials envisaged as a substitute for propylene, glycerol being able to be subjected to a catalytic dehydration reaction in order to produce acrolein. Such a process makes it possible to thus respond to the concept of green chemistry within a more general context of protecting the environment. There are also many possible ways to access to renewable glycerol, for example by fermentation of sugars or by hydrogenolysis reactions.

This process is highly analogous to the synthetic process starting from propylene insofar as the intermediate product, acrolein, resulting from the first stage is the same and insofar as the second stage is carried out under the same operating conditions.

However, the reaction of the first stage of the process of the invention, the dehydration reaction, is different from the reaction for the oxidation of propylene of the usual process. The dehydration reaction, performed in the gas phase, is carried out using different solid catalysts from those used for the oxidation of propylene. The acrolein-rich effluent resulting from the first dehydration stage, intended to feed the second stage of oxidation of acrolein to give acrylic acid, comprises a greater amount of water and in addition exhibits substantial differences as regards by-products resulting from the reaction mechanisms involved.

Numerous catalyst systems have already been the subject of studies for the dehydration reaction of glycerol to acrolein.

U.S. Pat. No. 5,387,720 describes a process for producing acrolein by dehydration of glycerol, in liquid phase or in gas phase, at a temperature ranging up to 340° C., over acidic solid catalysts that are defined by their Hammett acidity. The catalysts must have a Hammett acidity below +2 and preferably below −3. These catalysts correspond, for example, to natural or synthetic siliceous materials, such as mordenite, montmorillonite and acidic zeolites; supports, such as oxides or siliceous materials, for example alumina ($Al_2O_3$), titanium oxide ($TiO_2$), covered by monobasic, dibasic or tribasic inorganic acids; oxides or mixed oxides such as gamma-alumina, $ZnO/Al_2O_3$ mixed oxide, or else heteropolyacids. The use of these catalysts would make it possible to solve the problem of formation of secondary products generated with the iron phosphate type catalysts described in the document FR 695,931.

According to Application WO 06/087084, the strongly acidic solid catalysts whose Hammett acidity $H_0$ is between −9 and −18 have a strong catalytic activity for the dehydration reaction of glycerol to acrolein and are deactivated less quickly.

In the document WO 09/044,081 it has been proposed to carry out the reaction for dehydration of glycerol in the presence of a catalyst system comprising oxygen, iron, phosphorus, and one or more elements chosen from alkali metals, alkaline-earth metals, Al, Si, B, Co, Cr, Ni, V, Zn, Zr, Sn, Sb, Ag, Cu, Nb, Mo, Y, Mn, Pt, Rh and the rare earths La, Ce, Sm.

The document WO 09/128,555 describes a process for preparing acrolein by dehydration of glycerol in the presence of a catalyst comprising mainly a compound in which protons in a heteropolyacid are exchanged at least partially with at least one cation selected from elements belonging to Group 1 to Group 16 of the Periodic Table of Elements.

In the document WO 10/046,227 the dehydration of glycerol is performed in the presence of a catalyst system comprising oxygen, phosphorus and at least one metal chosen from vanadium, boron or aluminium.

However, the catalysts recommended in the prior art for producing acrolein from glycerol generally lead to the formation of by-products such as hydroxypropanone, propanaldehyde (called also propanal), acetaldehyde, acetone, addition products of acrolein to glycerol, polycondensation products of glycerol, cyclic glycerol ethers, and also phenol and polyaromatic compounds which are the source of the formation of coke on the catalyst and therefore of its deactivation.

The presence of the by-products in acrolein, especially propanal, poses numerous problems for the separation of acrolein and requires separation and purification steps which lead to high costs for the recovery of the purified acrolein. Furthermore, when acrolein is used for producing acrylic acid, the propanal present may be oxidized to propionic acid, which is difficult to separate from acrylic acid, especially by distillation. Indeed, propanal and propionic acid have their boiling points of respectively 49° C. and 141° C. which are very close to boiling points of 53° C. and 141° C. respectively of the objective compounds of acrolein and acrylic acid. The same problem occurs when acrolein is used to make methionine, or acetals or acrylonitrile, since the boiling points of acrylonitrile and propionitrile are respectively 77° C. and 97° C. These problems exist for the two means of production of acrolein/acrylic acid or acrylonitrile—from propylene or from glycerol—since propanal results as a by-product in the glycerol dehydration and in the propylene oxidation, but propanal is in a greater amount in the case of glycerol, probably owing to a lower selectivity of the reaction of dehydration of glycerol.

These impurities that are present greatly reduce the field of application of the acrolein and acrylic acid produced by dehydration of glycerol. In particular, impurities such as non-polymerizable saturated compounds can be particularly troublesome in the final application by modifying the properties of the finished product, by conferring toxic or corrosive properties on the finished product or by increasing polluting organic discharges during the stages of manufacture of the acrylic polymer and/or of the finished product.

Consequently, there is a need for an acrylic acid which meets all the above-mentioned constraints, both upstream, that is to say an acrylic acid essentially based on a non-fossil natural carbon source, and downstream, that is to say an acrylic acid which meets quality standards allowing it to be used in the manufacture of a broad range of technical polymers, without, however, requiring a sophisticated and therefore expensive purification.

To meet this need, it has already been proposed, for example in WO 09/044,081, to place two active catalyst beds in series: the gaseous reaction mixture containing glycerol is sent to a first catalyst in contact with which the dehydration reaction of glycerol is at least partially carried out generally resulting in secondary compounds such as propanal. The reaction mixture thus obtained is passed over a second catalyst bed such as a doped catalyst system based on iron phosphate, on which the dehydration reaction of unreacted glycerol may continue at the same time as the conversion of propanal to acrolein. The acrolein obtained according to this embodiment contains a minimized amount of propanal, which widens its field of application and facilitates obtaining high purity acrylic acid. However, it was observed that such catalysts lead to a rapid plugging of the facility due to the formation of products like tar.

The configuration of two active catalyst beds in series to limit the presence of propanal in acrolein has also been described in the process of WO 10/046,227 using a catalyst system based on a mixed oxide of phosphorus and vanadium. However, these catalysts are less active at moderate temperature.

The document WO 10/074,177 relates to a method for preparing acrylic acid from a composition containing acrolein and propanal by gas phase reaction using a solid catalyst comprising at least Mo and V as essential components. In this gas phase reaction, acrolein is converted to acrylic acid and propanal is converted to acrylic acid and to propionic acid. With this acrolein oxidation catalyst, propanal is converted at a similar rate as acrolein, and propanal is mainly converted to propionic acid. The conversion of propanal into acrylic acid is very low (3%), and the acrylic acid thus obtained contains a very high propionic acid content and it has to be purified by crystallization to remove propionic acid.

Also, it has been proposed to remove propionic acid from an acrylic acid stream, in particular from an acrylic acid mixed gas obtained by vapor-phase oxidation of propylene and/or propane, by reacting the acrylic acid stream in the presence of a mixed metal oxide containing at least Mo and/or Bi (JP 10-218831) or in the presence of a propionic acid reduction metal mixed oxide catalyst containing at least one element selected from the group of Mo and W (EP 2 039 674). These methods either involve a high temperature (300-500° C. in JP 10-218831), or lead to a significant loss of acrylic acid (more than 6% in EP 2 039 674).

Otherwise, the catalytic oxidative dehydrogenation of saturated aldehydes in unsaturated aldehydes is well known in prior art.

For example, Hargis et al, in I&EC product research and development, Vol 5, No. 1, March 1966, pp 72-75 propose to use an oxide of arsenic, antimony or bismuth to convert some saturated aldehydes into the corresponding unsaturated aldehydes. Propionaldehyde is converted into acrolein by using $Sb_2O_4$ as oxidant, but only with a selectivity of 62% for a conversion of 5%.

The oxydehydrogenation of saturated aldehydes to unsaturated aldehydes has been also described, more specifically for the production of methacrolein from isobutyraldehyde in U.S. Pat. No. 4,381,411, using iron phosphorous oxide containing at least one promotor. Conversion rates of 100% have been obtained for methacrolein yields ranging between 52% and 80%.

In Kinetics and Catalysis, Vol 44, No. 2, (2003) pp 198-201, isobutyraldehyde has been converted in methacrolein on a iron phosphate catalyst with a conversion of 80% and a selectivity of 82%. Moreover, it has been shown that the addition of a very small amount of molybdenum to Fe—P catalyst enhances the oxidation activity without modifying the high selectivity that originates from iron phosphate. This effect has not been studied in oxy-dehydrogenation of propanal into acrolein, but it has been observed that when the amount of molybdenum is larger that 4% in the catalyst, the selectivity falls, teaching a way to use molybdenum based catalyst.

The document JP 54-046705 discloses a process for preparing unsaturated aldehydes such as acrolein or methacrolein, and carboxylic acids such as acrylic acid or methacrylic acid, by the vapor phase oxidation of C3 and C4 saturated aldehydes such as propanal or isobutyraldehyde, in the presence of catalysts containing Mo, P oxides and one or two elements chosen among Zn, Cu or Ag, supported on a calcined carrier having a specific surface area of at least 10 $m^2/g$. In case of propanal, a yield of 53.1% of acrolein and acrylic acid is obtained at a conversion level of 72.6%, meaning that high conversion of propanal combined with a high selectivity in acrolein is difficult to obtain.

In Journal of Catalysis 195, 360-375 (2000), Ji Hu et al have studied the oxidative dehydrogenation of isobutyraldehyde to methacrolein over P—Mo catalyst. FIGS. 1 and 2 illustrate the effect of temperature on the reaction. They show that the conversion of isobutyraldehyde reaches a maximum of about 95% even at high temperature. It appears that it is difficult to convert more than about 95% of isobutyraldehyde without affecting the selectivity in methacrolein.

In React. Kinet. Catal. Lett. Vol 81, No. 2, 383-391 (2004), the same reaction have been studied over CsPMo catalyst by Cicmanec et al. FIGS. 3 and 4 illustrate the dependence of the conversion of isobutyraldehyde and the yield of methacrolein on contact time. It appears that the conversion is limited to 90% even with high contact time.

Prior art on the whole teaches away to convert saturated aldehydes present at low level in the corresponding unsaturated aldehydes since the man of the art would expect a degradation of the catalyst properties and a decrease of selectivity in unsaturated aldehydes.

In WO09/127,889, a 16.3% acrolein yield was obtained from glycerol at 91.3% conversion with a heteropolyacid containing molybdenum. It shows that heteropolyacids containing molybdenum are bad catalysts for the production of acrolein from glycerol. For that reason, the man of the art is not tempted to use those catalysts to eliminate propanal as an impurity in acrolein.

It is therefore an objective of the present invention to provide a process for selectively removing propanal as an impurity from an acrolein-rich stream without affecting acrolein. As a result, it has unexpectedly been found that the most selective catalysts for propanal elimination in an acrolein-rich stream comprise at least the element molybdenum.

It is another objective of the present invention to provide a process for manufacturing acrolein and/or acrylic acid containing low amount of propanal and/or propionic acid.

It is another objective of the present invention to provide a process for manufacturing acrylic acid from glycerol including a step of selective elimination of propanal, while providing acrylic acid essentially based on a non-fossil natural carbon source and overcoming the drawbacks of the existing catalysts for the dehydration of glycerol.

SUMMARY OF THE INVENTION

One subject of the present invention is therefore a process for manufacturing acrolein characterized in that it comprises selective elimination of propanal in an acrolein-rich stream by passing the said stream in gas phase in the presence of oxygen through a catalyst comprising at least molybdenum and at least one element selected from P, Si, W, Ti, Zr, V, Nb, Ta, Cr, Mn, Fe, Co, Ni, Cu, Zn, Ga, In, Tl, Sn, Ag, As, Ge, B, Bi, La, Ba Sb Te, Ce, Pb.

In the present invention, "selective" means that propanal is more converted than acrolein on the bed of catalyst and that propanal is not converted into propionic acid to an extent higher than 50%. The conversion (%) of a material is defined as the ratio between the mole number of material reacted on the catalyst divided by the mole number of material supplied to the catalyst.

The acrolein-rich stream in the present invention may be produced by any conventional technique known by those of ordinary skill in the art. Additionally, any conventional raw material feed may be used to produce acrolein so long as the acrolein product stream contains some amount of propanal.

Another subject of the invention is a process for manufacturing acrylic acid comprising the oxidation of acrolein obtained after elimination of propanal according to the above-mentioned process.

Another subject of the invention is a process for manufacturing acrylonitrile comprising the ammoxidation of acrolein obtained after elimination of propanal according to the above-mentioned process.

Another subject of the invention is a process for manufacturing methylmercaptopropionaldehyde used for producing methionine, comprising the addition of methyl mercaptan to acrolein obtained after elimination of propanal according to the above-mentioned process.

The present invention provides further a process for manufacturing bio-sourced acrylic acid containing a low amount of propionic acid from glycerol, which is a raw material independent of petroleum.

The invention will be more clearly understood on reading the following detailed description, from the non-limiting examples of embodiments thereof.

DETAILED DESCRIPTION

The catalyst for selective elimination of propanal used in the process of the invention comprises at least molybdenum.

Advantageously, the process for manufacturing acrolein is characterized in that it comprises selective elimination of propanal in an acrolein-rich stream by passing the said stream in gas phase in the presence of oxygen through a catalyst comprising at least molybdenum and at least one element selected from P, Si, W, Ti, Zr, V, Nb, Ta, Cr, Mn, Fe, Co, Ni, Cu, Zn, Ga, In, Tl, Sn, Ag, As, Ge, B, Bi, La, Ba Sb Te, Ce, Pb, chosen in the group formed by the mixed metal oxides containing at least molybdenum and heteropolyacids containing at least molybdenum.

In one embodiment of the invention, the catalyst comprises at least molybdenum and a single element selected from P, Si, W, Ti, Zr, V, Nb, Ta, Cr, Mn, Fe, Co, Ni, Cu, Zn, Ga, In, Tl, Sn, Ag, As, Ge, B, Bi, La, Ba Sb Te, Ce, Pb.

In one embodiment, the catalyst according to the invention may be a mixed metal oxide based on molybdenum that is used with other feedstocks than saturated aldehyde, for example for methanol oxidation to formaldehyde (Fe—Mo—O doped or not) and propylene oxidation to acrolein (based on bismuth molybdate, for example with a general formula described in EP 1987877: $Mo_{12}Bi_aFe_bA_cB_dC_eD_fO_x$ wherein A is at least an element selected from cobalt and nickel, B is at least an element selected from alkali metals, alkaline earth metals and thallium, C is at least an element selected from tungsten, silicon, aluminum, zirconium and titanium; D is at least an element selected from phosphorus, tellurium, antimony, tin, cerium, lead, niobium, manganese, arsenic and zinc, potassium).

Examples of Fe—Mo—O iron molybdate catalysts are described in Catalysis Review, Vol 47 (2004), pp 125-174.

Iron molybdenum based catalysts are commercially available. For example Süd Chemie supplies several grades of such catalysts under the trade name FAMAX®: FAMAX J5, FAMAX MS, FAMAX HS, FAMAX TH.

Examples of propylene oxidation catalysts to acrolein are described in EP 900774, EP 1125911, EP 1987877, EP 1074938, U.S. Pat. No. 6,268,529, U.S. Pat. No. 4,837,940.

Preferably, the catalyst comprises molybdenum and at least one element selected from P, Si, W, Cr, Mn, Fe, Co, Ni, Bi, Sb, Ce.

In one embodiment, the catalyst according to the invention comprises at least one heteropolyacid containing at least molybdenum.

Advantageously, proton in the heteropolyacid containing at least molybdenum, may be partially exchanged by at least one cation selected from elements belonging to Group 1 to 16 of the Periodic Table of elements.

The catalyst according to the invention may be represented by the general formula:

$$A_a X_b Y_c Z_d O_e$$

in which

A is more than one cation selected from elements belonging to Group 1 to 16 of the Periodic Table of Elements and lanthanides, preferably one alkali metal cation such as cesium, rubidium or potassium.

X is P or Si, preferably P

Y is Mo

Z is more than one element selected from the group comprising W, Ti, Zr, V, Nb, Ta, Cr, Mn, Fe, Co, Ni, Cu, Zn, Ga, In, Tl, Sn, Ag, As, Ge, B, Bi, La, Ba, Sb, Te, Ce and Pb, preferably Fe, Bi, Co, Ni, W, V, Cr, Sb, Mn, Ce a, b, c and d satisfying following ranges:

$0 \le a \le 9$, preferably $0 < a \le 9$ $0 \le b \le 2$ preferably $0.1 \le b \le 1.5$ $0 < c \le 12$ preferably $5 < c \le 12$ $0 \le d < 12$ preferably $0 \le d \le 4$ and e is a number determined by the oxidation of the elements.

Examples of effective catalysts are mixed oxides or heteropolyacid salts of FeMo, CsPMo, CsPWMo or BiMoFe catalysts.

The catalyst used in the present invention can be prepared by any known technique, for example as described in WO/09/128,555 (heteropolyacids) or in Catalysis Review, Vol 47 (2004), pp 125-174 and the references described therein. Generally, the resulting solid component is finally fired or calcined to obtain the catalyst for selective elimination of propanal according to the present invention.

The calcination can be carried out in air or under inert gas such as nitrogen, helium and argon or under an atmosphere of mixed gas of oxygen and inert gas, usually in a furnace such as muffle furnace, rotary kiln, fluidized bed furnace. Type of the furnace is not limited specially. The calcination can be effected even in a reaction tube that is used for the glycerin dehydration reaction. The firing temperature is usually 150 to 900° C., preferably 200 to 800° C. and more preferably 200 to 600° C. The calcination is continued usually for 0.5 to 10 hours.

The catalyst in the process according to the invention may be a bulk and is used, in this case, without any support.

The catalyst may also be loaded on a support (or carrier), the amount of support generally representing from 0 to 90%, preferably at least 5% of the total weight of the catalyst.

The carrier can be granule and powder and may have any shape such as sphere, pellet, cylindrical body, hollow cylinder body, trilobe and quadrilobe and bar with optional molding aid.

It is possible to use, as a support, any material such as silica, alumina, magnesia, titanium oxide, zirconia, silicon carbide, silica/alumina mixture, silicates, diatomaceous earth, borates or carbonates on condition that these products are stable under the reaction conditions to which the catalyst will be subjected. Preferably, the catalyst is not a supported catalyst.

The catalyst may have any shape and can be granule or powder. It is preferable to mold the catalyst into a shape of sphere, pellets, cylinder, hollow cylinder, bar or the like, optionally with adding a molding aid. The catalyst can be shaped into the above-configurations together with carrier and optional auxiliary agents. The molded catalyst may have a particle size of for example 1 to 10 mm for a fixed bed and of less than 1 mm for a fluidized bed.

The acrolein-rich stream in the process according to the invention can be specifically the product stream of a propylene (or other non-petroleum based sources of hydrocarbons) catalytic oxidation process, or the product stream of glycerol dehydration in liquid phase or in gas phase, preferably in gas phase or in a stream of hydroxypropanal dehydration. Generally, the acrolein-rich stream results as a gas mixture that is submitted directly for the process according to the invention Examples of operating conditions for dehydrating glycerol into acrolein are described in the international patent applications WO 06/087083, WO 06/087084, WO 09/128,555 or WO 10/046,227 of the Applicant. Specifically, the catalyst used for the reaction of dehydration is a catalyst having Hammett acidity lower than +2. Specifically, the catalyst used for the reaction of dehydration is a catalyst containing no molybdenum.

Examples of operating conditions for oxidation of propylene into acrolein are described in Process Economic Program n° 6D from SRI consulting and the reference cited therein.

The amount of propanal in the acrolein-rich stream is generally less than 0.2, expressed by the moles of propanal relative to the moles of acrolein present in the stream. It may range from 1/4000 to 1/5 expressed by the moles of propanal relative to the moles of acrolein present in the stream, preferably from 1/1000 to 1/10.

The acrolein-rich stream in the process according to the invention contains water, oxygen, and eventually by-products such as hydroxypropanone, acetaldehyde, acetone, addition products of acrolein to glycerol, polycondensation products of glycerol, cyclic glycerol ethers, hydroxypropanal, phenol and polyaromatic compounds, propylene, acrylic acid, and inert gases such as carbon oxide, carbon dioxide, nitrogen, helium, argon, propane. The nature of the by-products and the composition of the acrolein-rich stream depend of course on the raw material used to produce acrolein.

Thus, in the case where propylene is the main raw material in an oxidation reaction to produce acrolein, the acrolein-rich stream may contain propane as thermal ballast.

In the case where glycerol is the main raw material in a dehydration process to produce acrolein, the mixture of acrolein and propanal may contain a large amount of water depending of the concentration of glycerol in the feed.

In the process according to the invention, the concentration of acrolein in the gas mixture that is passed through the catalyst ranges from 1 to 12 mole %, preferably from 4 to 10 mole %.

The process according to the invention is carried out in the presence of oxygen, or an oxygen-containing gas such as air. Generally, oxygen is already present in the gas mixture, but further oxygen may be injected if the oxygen concentration is too low. Oxygen content is comprised between 1 and 10% (mol) and preferably between 3 and 7% (mol).

The concentration of water of the acrolein-rich stream may vary largely. Water content is comprised between 3 and 90% (mol) and preferably between 8 and 80% (mol).

The selective elimination of propanal operates at a temperature between 250° C. and 400° C., preferably between 280 and 350° C., and at a pressure between 1 and 5 bar absolute and preferably between 1 and 2 bar.

A feed rate of the gas reactant is advantageously 1000 to 40,000 h$^{-1}$ in term of GHSV (gas hourly space velocity in normal m$^3$/h/volume of catalyst in m$^3$), preferably 3000 to 30000 h$^{-1}$, more preferably 5000 to 20000 h$^{-1}$. If the GHSV becomes lower than 1000 h$^{-1}$, the selectivity will be lowered. On the contrary, if the GHSV exceeds 40,000 h$^{-1}$, the conversion will be lowered.

For each catalyst there is an optimum of temperature and GHSV for which a high conversion of propanal is obtained at a low conversion of acrolein.

The selective elimination of propanal in an acrolein-rich stream according the invention can be carried out in a variety of reactors such as fixed bed, fluid bed, circulating fluid bed and moving bed. Among them, the fixed bed and the fluid bed are preferable.

When a fluid bed or circulating fluid bed reactor is used as a first reactor for the production of the acrolein-rich stream, the propanal elimination catalyst can be used as a fixed bed downstream of the said first reactor, or it can be used as a compartmentalized fluid bed reactor. This type of reactor can be made by using a grid or a mesh within the fluid bed that keep the first catalyst in the lower part of the fluid bed and the propanal elimination catalyst in the upper part of the fluid bed.

In a first embodiment of the invention, the production of the acrolein-rich stream and the selective elimination of propanal are carried out in a tandem-type reactor comprising two reactors linked to each other, where the two reactors are filled with a catalyst for the production of acrolein and a catalyst for the selective elimination of propanal respectively, and where the production of acrolein and the elimination of propanal are separately conducted in their respective reactors.

In a second embodiment of the invention, the production of the acrolein-rich stream and the selective elimination of propanal are carried out in a single-reactor-type, where the reactor filled with a catalyst for the selective elimination of propanal on the reaction gas outlet side and with a catalyst for the production of acrolein on the reaction gas inlet side, thus conducting in the single reactor the production of acrolein followed by the selective elimination of propanal. It is preferable that the reactor has different zone of temperature control so that elimination of propanal can be operated at a different temperature from the production of acrolein. In case of a fixed bed reactor, a preferred configuration is when the gas is moving upward through the bed and the propanal elimination catalyst is placed on top of the catalyst for the production of acrolein.

In the case of fixed beds, when a multitubular reactor is used for the acrolein production a preferred configuration for the selective elimination of propanal is a layer of catalyst on top of the tubular plate, above the reactor tubes containing the acrolein producing catalyst. This configuration is preferred to replace more easily the propanal elimination catalyst by vacuum unloading.

Acrolein thus obtained by the process according to the invention contains less than 5000 ppm, even less than 1000 ppm of propanal.

Another subject of the invention is the use of a catalyst comprising at least molybdenum and at least one element selected from P, Si, W, Ti, Zr, V, Nb, Ta, Cr, Mn, Fe, Co, Ni, Cu, Zn, Ga, In, Tl, Sn, Ag, As, Ge, B, Bi, La, Ba Sb Te, Ce, Pb, chosen in the group formed by the mixed metal oxides containing at least molybdenum and heteropolyacids containing at least molybdenum, to reduce the content of propanal lower than 5000 ppm, preferably lower than 1000 ppm, in an acrolein-rich stream.

Acrolein obtained by the process according to the invention can be advantageously further subjected to known oxidation methods to produce acrylic acid with a low content of propionic acid, typically containing less than 5000 ppm, even less than 1000 ppm of propionic acid, which is a typical specification level for a broad range of applications.

Thus, another subject of the invention is the use of a catalyst comprising at least molybdenum and at least one element selected from P, Si, W, Ti, Zr, V, Nb, Ta, Cr, Mn, Fe, Co, Ni, Cu, Zn, Ga, In, Tl, Sn, Ag, As, Ge, B, Bi, La, Ba Sb Te, Ce, Pb, chosen in the group formed by the mixed metal oxides containing at least molybdenum and heteropolyacids containing at least molybdenum to produce acrylic acid with a low content of propionic acid, typically containing less than 5000 ppm, even less than 1000 ppm of propionic acid.

Generally, the oxidation reaction is carried out in the presence of molecular oxygen or of a mixture comprising molecular oxygen, at a temperature ranging from 200° C. to 350° C., preferably from 250° C. to 320° C., and under a pressure ranging from 1 to 5 bar, in the presence of an oxidation catalyst comprising at least one element chosen from the list Mo, V, W, Re, Cr, Mn, Fe, Co, Ni, Cu, Zn, Sn, Te, Sb, Bi, Pt, Pd, Ru and Rh, present in the metallic form or in the oxide, sulfate or phosphate form. Use is made in particular of the formulations comprising Mo and/or V and/or W and/or Cu and/or Sb and/or Fe as main constituents. The oxidation catalyst may be supported on a carrier such as zirconia, silica, alumina, steatite and combination thereof and silicon carbide. Acrolein gas stream contains the same kind of components as the selective elimination step of propanal, such as water, or inert gases such as carbon oxide, carbon dioxide, nitrogen, helium, argon, propane or organic impurities.

Acrolein obtained by the process according to the invention can be advantageously further subjected to known ammoxidation methods to produce acrylonitrile with a low content of propionitrile, typically containing less than 5000 ppm, even less than 1000 ppm of propionitrile, which is a typical specification level for a broad range of applications.

Acrolein obtained by the process according to the invention can be advantageously further subjected to known condensation reaction to produce glutaraldehyde, for example according to the process described in the document WO 2011/055051.

Acrolein obtained by the process according to the invention can be advantageously further subjected to known addition with methyl mercaptan to produce methylmercaptopropionaldehyde used for manufacturing methionine or its salt or its hydroxyl analogue, 2-hydroxy-4-methylthio-butyric acid. Advantageously, acrolein is purified by absorption in water and further distillation before being reacted with methylmercaptan to yield methylmercaptopropionaldehyde. Insofar as propanal amount is reduced to a minimum value, methylmercaptopropionaldehyde can be used without purification for the production of methionine or its salt or its hydroxy analogue.

Another object of the present invention is a process for manufacturing acrylic acid from glycerol characterized in that it comprises at least the following steps:

a) dehydration of glycerol to give an acrolein-rich stream containing propanal, b) selective elimination of propanal by passing the said stream in gas phase in the presence of oxygen through a catalyst comprising at least molybdenum and at least one element selected from P, Si, W, Ti, Zr, V, Nb, Ta, Cr, Mn, Fe, Co, Ni, Cu, Zn, Ga, In, Tl, Sn, Ag, As, Ge, B, Bi, Cr, La, Ba Sb Te, Ce, Pb;

c) oxidation of the acrolein to give acrylic acid.

The first step a) may be carried out in the gas phase or in the liquid phase, preferably in the gas phase. When the dehydration reaction is carried out in the gas phase, various process technologies may be used, namely a fixed bed process, with one or several reactors in parallel, a fluid bed process or a circulating fluid bed process. It is also possible to use reactors of the plate heat exchange type.

The experimental conditions of the gas-phase reaction are preferably a temperature between 180° C. and 500° C., preferably between 250 and 400° C. and a pressure between 1 and 5 bars. In the liquid phase, the reaction is preferably carried out at a temperature between 150° C. and 350° C. and a pressure which may range from 3 to 70 bar.

Use is generally made of glycerol, or a mixture of glycerol and water having a weight ratio which can vary within wide limits, for example from 0.1 to 100, preferably between 0.5 and 4, in the reactor.

The mixture of glycerol and water may be used in liquid form or in gaseous form, preferably in the gas phase form.

According to one embodiment of the invention, it is possible to use >95% pure glycerol, that is to say with <5% water, and to blend the said glycerol with a gas mixture comprising vaporized water and inert gas, possibly coming form a recycle gas, so as the reaction of converting glycerol into acrolein is conducted in gas phase.

Preferably, the step a) is carried out in the presence of oxygen, or an oxygen-containing gas, as described in applications WO 06/087083 or WO 06/114506. The molar ratio of the molecular oxygen to the glycerol is generally around 0.1 to 1.5, preferably from 0.5 to 1.0.

The glycerol dehydration reaction is generally carried out over solid acid catalysts. The catalysts that are suitable are homogeneous or heterogeneous substances which are insoluble in the reaction medium and which have a Hammett acidity, denoted $H_0$, of less than +2. The catalyst will be chosen among suitable catalysts containing no molybdenum.

A key parameter lies in the concentration of glycerol in the charge. Expressed in mole percent, the concentration of glycerol varies widely from 0.1 to 20. As is common in reactions of this type, the yield of the desired product is an inverse function of the concentration. From the point of view of obtaining a reasonable flow rate combined with an acceptable yield, the concentration of glycerol in the charge is around 3 to 16 mol %. The concentration is controlled by the amount of water and of inert gas present in the feed stream. The preferred gaseous diluent is nitrogen although other gases such as carbon dioxide, helium, argon, etc. are also suitable. Of course, when the desired concentration of glycerol permits it, air represents a suitable diluted oxidant.

The contact time expressed in seconds is the ratio between the volume of the catalyst bed and the volume (corrected for normal pressure and normal temperature) of the gaseous reactants conveyed per second. The average temperature and pressure conditions in a bed may vary depending on the nature of the catalyst, the nature of the catalyst bed and the size of the catalyst. In general, the contact time is from 0.1 to 20 seconds and preferably from 0.3 to 15 seconds.

In the process for manufacturing acrylic acid from glycerol of the invention, the step b) consists in the selective elimination of propanal according to the above-described process, in the acrolein-rich stream coming from the step a) to give an acrolein-rich stream with a low content of propanal, further oxidized in step c) into acrylic acid.

Preferably, the catalyst used in the step b) is chosen in the group formed by the mixed metal oxides containing at least molybdenum and heteropolyacids containing at least molybdenum.

The gas mixture resulting from the step c) is composed, apart from acrylic acid:

of light compounds which are non-condensable under the temperature and pressure conditions normally employed: nitrogen, unconverted oxygen, carbon monoxide and carbon dioxide, which are formed in a small amount by final oxidation or by recycled in the process, of condensable light compounds: in particular water, generated by the dehydration reaction or present as diluent, unconverted acrolein, light aldehydes, such as formaldehyde and acetaldehyde, formic acid and acetic acid, of heavy compounds: furfuraldehyde, benzaldehyde, maleic acid, maleic anhydride, benzoic acid, 2-butenoic acid, phenol, protoanemonin, and the like.

Then, the process for manufacturing acrylic acid according the invention further comprises the steps of collecting the resultant acrylic acid as a solution by using water or a solvent, and then of purifying the resultant solution containing acrylic acid by using for example a distillation step for removing low- and high-boiling point materials and/or a crystallization step for purifying acrylic acid by crystallizing it.

The acrylic acid thus obtained can be used to produce for example polyacrylic acids or salts as water-soluble polymers or water-absorbent resins, by known methods.

According to one particular embodiment of the invention, use is made of an intermediate step of partial condensation of water and of the heavy by-products derived from the dehydration step a), as is described for example in the patent application WO 08/087,315.

The said intermediate step has the aim of removing most of the water present and the heavy by-products before sending the gaseous stream comprising the acrolein and all non-condensable gases to the propanal elimination step or to the step for the oxidation of acrolein to give acrylic acid. This partial condensation of the water thus makes it possible to avoid damage to the catalyst of the oxidation of acrolein to give acrylic acid and to avoid, during the subsequent stages, the removal of large amounts of water, which could well be expensive and result in losses of acrylic acid. In addition, it makes it possible to remove a portion of the "heavy" impurities formed during the dehydration of the glycerol and to facilitate purification operations.

This intermediate step is carried out on a separating unit which is a condensation plant comprising an absorption column coupled or not coupled to an evaporator, one or more heat exchangers, one or more condensers, a dephlegmator, and any item of equipment well known to a person skilled in the art which makes it possible to carry out a partial condensation of an aqueous stream.

It is carried out under conditions such that the acrolein-rich stream is separated into an acrolein-rich gaseous phase and an acrolein-poor aqueous phase.

From 20 to 95%, preferably from 40 to 90%, of the water present in the stream is removed in the liquid stream and the acrolein-rich phase generally comprises more than 80% and preferably more than 90% of the acrolein initially present in the stream This result is generally obtained by lowering the temperature to a temperature of 60 to 120° C.

In one embodiment, the step of partial condensation of water and of the heavy by-products derived from the dehydration step a) is carried out before operating the step b) of selective elimination of propanal. In this embodiment, it is preferred that the catalyst for propanal elimination and the catalyst for the oxidation of acrolein into acrylic acid are installed in the same reactor. Generally two separate reaction zones with two separate cooling systems are used for the 2 catalysts. It is also possible that catalysts are operated in 2 separate reactors.

In an alternative form, the step of partial condensation of water and of the heavy by-products derived from the dehydration step a) is carried out after operating the step b) of selective elimination of propanal. In this embodiment, propionic acid derived from the dehydration reaction and the propanal elimination reaction may be easily removed by the partial condensation of water from the acrolein-rich stream before the oxidation stage. As most part of acrylic acid is also removed by the partial condensation of water, reaction conditions are chosen to limit as far as possible the conversion of acrolein in the propanal elimination step.

According to the process of the invention, it is possible to obtain acrylic acid having a content of propionic acid lower than 500 ppm.

Now, the present invention will be explained in much detail with referring several examples, but this invention should not be limited to those described in following examples. In the following Examples and Comparative Examples, % means mole %.

EXAMPLES

Preparation of Catalyst

Example 1

CsPMo 100 g of phosphomolybdic acid was dissolved in 200 mL of deionized water to obtain an aqueous solution of phosphomolybdic acid, and then was mixed at room temperature for 2 hours.
32.7 g of 48.5 wt % CsOH aqueous solution was diluted with 20 mL of deionized water. The resulting CsOH aqueous solution was dropped in the above aqueous solution of phosphomolybdic acid, and then was mixed at room temperature for 2 hours.
The resulting yellow slurry was evaporated at 60° C. by use of rotary-evaporator.
The obtained powder was dried at 120° C. for 10 hours.
The composition of the resultant dried slurry is:

$Cs_{2.5}P_{1.0}Mo_{12}$

Subsequently, the resultant product was calcined in air at 250° C. for 3 hours.

Example 2

CsPWMo 50 g of phosphotungstomolybdic acid was dissolved in 20 mL of deionized water to obtain an aqueous solution of phosphotungstomolybdic acid, and then was mixed at room temperature for 2 hours.

13.4 g of 48.5 wt % CsOH aqueous solution was diluted with 50 mL of deionized water. The resulting CsOH aqueous solution was dropped in the above aqueous solution of phosphotungstomolybdic acid, and then was mixed at room temperature for 2 hours.
The resulting yellow slurry was evaporated at 60° C. by use of rotary-evaporator. The obtained powder was dried at 120° C. for 10 hours.
The composition of the resultant dried slurry is:

$Cs_{2.5}P_{1.0}W_6Mo_6$

Subsequently, the resultant product was calcined in air at 250° C. for 3 hours.

Example 3

MoVPCuAs 100 g of molybdenum trioxide, 6.3 g of vanadium pentoxide, 1.1 g of copper oxide and 8.0 g of 85 wt % orthophosphoric acid and 1.8 g of 60 wt % arsenic acid were dispersed in 1000 mL of deionized water. The mixture was refluxed for 6 hours while adding hydrogen peroxide to yield a reddish-brown, transparent solution. After a little insoluble compound was removed from the obtained solution, the solution thus formed was evaporated to dryness on a water bath.
The composition of the dried product is:

$Mo_{10}V_{1.0}P_{1.0}Cu_{0.2}As_{0.2}$

Subsequently, the resultant product was calcined under a flow of air at 310° C. for 5 hours.

Example 4

MoVPCuAsSb 300 g of molybdenum trioxide, 11.37 g of vanadium pentoxide, 3.31 g of copper oxide, 8.32 g of copper acetate, 28.82 g of 85 wt % orthophosphoric acid and 24.64 g of 60 wt % arsenic acid were dispersed in 1900 mL of deionized water and heated at reflux at 95 to 100° C. for six hours to yield a reddish-brown, transparent solution. Subsequently, to the solution was added 1.52 g of antimony trioxide and the resultant solution was further heated at reflux at 95 to 100° C. for three hours.
Then, the resultant slurry was heated in a water bath to be evaporated and dried.
The composition of the dried product is:

$Mo_{10}V_{0.6}P_{1.2}Cu_{0.4}As_{0.5}Sb_{0.05}$

Subsequently, the resultant product was calcined under a flow of air at 310° C. for 5 hours.

Example 5

MoVPCuSbCs

To 1200 mL of purified water were added 200 g of molybdenum trioxide, 8.84 g of vanadium pentaoxide and 17.61 g of 85 wt % orthophosphoric acid, and the solution was heated at reflux at 90 to 100° C. for five hours to yield a reddish-brown, transparent solution.
Subsequently, to the solution was added 6.07 g of antimony trioxide and the resultant solution was further heated at reflux at 90 to 100° C. for two hours to obtain an antimony trioxide-dissolved, highly dark blue solution.
Then, the resulting solution was cooled to from 15 to 20° C. To the solution were gradually added a solution of 13.33 g of cesium acetate dissolved in 150 mL of purified water and a solution of 16.06 g of ammonium acetate dissolved in 150 mL of purified water at the same time with agitation. Then, to the slurry was further added a solution prepared by dissolving 11.09 g of cupric acetate monohydrate in 170 mL of purified water and the resultant solution was aged at 15 to 20° C. for one hour to yield a green blue slurry. Then, the resultant slurry was heated in a water bath to be evaporated and dried. The composition of the resultant dried slurry is:

$Mo_{10}V_{0.7}P_{1.1}Cu_{0.4}Sb_{0.3}Cs_{0.5}(NH_4)_{1.5}$

Subsequently, the resultant product was calcined under a flow of air at 310° C. for 5 hours.

Evaluation and Results

Example 6

Selective Elimination of Propanal in an Acrolein Flow

A sample of CsPMo catalyst from example 1 was compacted and crushed and sieved to obtain particle size of 35 to 48 mesh. A stainless steel tube (internal diameter 13 mm) was loaded with 2.0 ml of catalyst to form a fixed catalytic bed. An aqueous solution of acrolein and propanal was fed to an evaporator together with nitrogen and with oxygen at 270° C. in order to form a feed gas which was passed through the fixed catalytic bed at atmospheric pressure. The fixed catalytic bed was heated with an electric oven at a temperature of 270° C. Feed gas had a following composition in mol %: acrolein:propanal:oxygen:nitrogen:water=6.0:0.060:3.8:14:76. Total feed gas flow was 31 normal liter per hour. Gas Hourly Space Velocity (GHSV) was 15,000 h$^{-1}$. GHSV is the ratio of the flow of feed gas (expressed in normal liter per hour) by the volume of catalyst (expressed in liter). Fixed bed was operated for 5 hours without pressure increase in the reactor.
In order to characterize the composition of the gas flow out the reactor, products were condensed in a condenser charged with demineralized water. Liquid aqueous phase and gaseous vents were quantitatively analyzed by gas chromatographs (HP 6890 Agilent, FFAP column, FID detector, CP4900 Varian, Silicaplot and Molecular Sieve 5 Å, TCD detectors). Proportions of products were corrected in factors from the results of the gas chromatograph to determine absolute amounts of products.
The conversion (%) of material (acrolein or propanal), and the yield of objective substance (%) and the relative rate of conversion are determined by following equations:

The conversion (%) of material=(mole number of material reacted/mole number of material supplied)×100

The yield (%) of acrylic acid=(mole number of acrylic acid obtained/mole number of acrolein supplied)×100

The yield (%) of propionic acid=(mole number of propionic acid obtained/mole number of propanal supplied)×100

The relative rate of propanal elimination=conversion of propanal/conversion of acrolein Results are shown in table 1.

Example 7

The same experiment as in example 6 was reproduced, with a gas hourly space velocity of 14,000 h$^{-1}$ and vaporizer and oven temperatures of 300° C. Fixed bed was operated for 5 hours without pressure increase in the reactor.
Results are shown in table 1.

Example 8

The same experiment as in example 6 was reproduced, with a gas hourly space velocity of 4,400 h$^{-1}$ and vaporizer and oven temperatures of 270° C. Fixed bed was operated for 5 hours without pressure increase in the reactor.
Results are shown in table 1.

Example 9

The same experiment as in example 6 was reproduced, with a gas hourly space velocity of 4,400 h$^{-1}$ and vaporizer and oven temperatures of 300° C. Fixed bed was operated for 5 hours without pressure increase in the reactor.
Results are shown in table 1.

Example 10

The same experiment as in example 6 was reproduced, with CsPWMo catalyst of example 2 and with a gas hourly space velocity of 5,500 h$^{-1}$ and vaporiser and oven temperatures of 250° C. Fixed bed was operated for 5 hours without pressure increase in the reactor.
Results are shown in table 1.

Example 11

The same experiment as in example 6 was reproduced, with MoVPCuAs catalyst of example 3 and with a gas hourly space velocity of 5,000 h$^{-1}$ and vaporiser and oven temperatures of 350° C. Fixed bed was operated for 5 hours without pressure increase in the reactor.
Results are shown in table 1.

TABLE 1

| Example | 6 | 7 | 8 | 9 | 10 | 11 |
|---|---|---|---|---|---|---|
| Catalyst | CsPMo | CsPMo | CsPMo | CsPMo | CsPWMo | MoVPCuAs |
| GHSV h$^{-1}$ | 15,000 | 14,000 | 4,400 | 4,400 | 5,500 | 5,000 |
| Vaporiser and oven temperature (° C.) | 270 | 300 | 270 | 300 | 250 | 350 |
| Propanal conversion (%) | 90 | 82 | 99 | 100 | 92 | 65 |
| Propionic acid yield (%) | 10 | 12 | 11 | 9 | 13 | 15 |
| Acrolein conversion (%) | 11 | 25 | 28 | 65 | 53 | <5 |
| Acrylic acid yield (%) | 7 | 22 | 13 | 64 | 36 | 5 |
| Propanal elimination (relative rate) | 7.9 | 3.2 | 3.5 | 1.5 | 1.7 | >13 |

Example 12

The same experiment as in example 6 was reproduced, with MoVPCuAs catalyst of example 3 and with a gas hourly space velocity of 4,700 h$^{-1}$ and vaporiser and oven temperatures of 385° C. Fixed bed was operated for 5 hours without pressure increase in the reactor.
Results are shown in table 2.

Example 13

The same experiment as in example 6 was reproduced, with MoVPCuAsSb catalyst of example 4 and with a gas hourly space velocity of 4,400 h$^{-1}$ and vaporiser and oven temperatures of 345° C. Fixed bed was operated for 5 hours without pressure increase in the reactor.
Results are shown in table 2.

Example 14

The same experiment as in example 6 was reproduced, with MoVPCuSbCs of example 5 and with a gas hourly space velocity of 5,500 h$^{-1}$ and vaporiser and oven temperatures of 250° C. Fixed bed was operated for 5 hours without pressure increase in the reactor. Results are shown in table 2.

TABLE 2

| Example | 12 | 13 | 14 |
|---|---|---|---|
| Catalyst | MoVPCuAs | MoVPCuAsSb | MoVPCuSbCs |
| GHSV h$^{-1}$ | 4,700 | 4,400 | 5,500 |
| Vaporiser and oven temperature (° C.) | 385 | 345 | 250 |
| Propanal conversion (%) | 97 | 14 | 98 |
| Propionic acid yield (%) | 14 | 14 | 13 |
| Acrolein conversion (%) | 23 | <5 | 29 |
| Acrylic acid yield (%) | 20 | 1 | 15 |
| Relative rate of propanal elimination | 4.2 | >3 | 3.4 |

Example 15

The same experiment as in example 6 was reproduced, with FeMo catalyst from MAPCO, reference MFM3-MS, and with a gas hourly space velocity of 10,000 h$^{-1}$ and vaporiser and oven temperatures of 305° C. Fixed bed was operated for 5 hours without pressure increase in the reactor.
Results are shown in table 3.

Example 16

The same experiment as in example 15 was reproduced, with a gas hourly space velocity of 20,000 h$^{-1}$ and vaporiser and oven temperatures of 330° C. Fixed bed was operated for 5 hours without pressure increase in the reactor.
Results are shown in table 3.

Example 17

The same experiment as in example 16 was reproduced, with a feed gas composition in mol %:acrolein:propanal:oxygen:nitrogen:water=6.2:0.062:6.7:69:18. In this experiment a much lower concentration of water was used compared to example 16. Fixed bed was operated for 5 hours without pressure increase in the reactor.
Results are shown in table 3.

Example 18

The same experiment as in example 6 was reproduced, with propylene oxidation catalyst based on BiMoFe that was prepared according to example 1 of European Patent EP 807 465 B1. Gas hourly space velocity was 5,800 h$^{-1}$ and vaporiser and oven temperatures were set to 325° C. Fixed bed was operated for 5 hours without pressure increase in the reactor.
Results are shown in table 3.

Example 19

Comparative

The same experiment as in example 6 was reproduced with TiO$_2$ catalyst (ST31119 from Norpro saint Gobain). Fixed bed was operated for 5 hours without pressure increase in the reactor.
The same experiment was also reproduced with a gas hourly space velocity of 3,700 h$^{-1}$ and vaporiser and oven temperatures of 300° C. Fixed bed was operated for 5 hours without pressure increase in the reactor.
Results are shown in table 3.
We observed that propanal is not selectively eliminated as acrolein is more converted than propanal.

TABLE 3

| | Example | | | | | |
|---|---|---|---|---|---|---|
| | 15 | 16 | 17 | 18 | 19 (Comparative) | |
| Catalyst | | FeMo | | BiMoFe | TiO$_2$ | |
| GHSV h$^{-1}$ | 10,000 | 20,000 | 20,000 | 5,800 | 15,000 | 3,700 |
| Vaporiser and oven temperature (° C.) | 305 | 330 | 330 | 325 | 270 | 300 |
| Propanal conversion (%) | 98 | 99 | 99 | 96 | <5 | 16 |
| Propionic acid yield (%) | 3 | 6 | 6 | 8 | 0 | 8 |
| Acrolein conversion (%) | 9 | <6 | 11 | <5 | <5 | 30 |
| Acrylic acid yield (%) | 0.5 | 2 | 2 | 3 | 0 | 1 |
| Relative rate of propanal elimination | 11 | >15 | 9 | >19 | | 0.6 |

Example 20

Comparative

The same experiment as in example 6 was reproduced with FePSr catalyst prepared according to example 3 of WO2009/44081, with a gas hourly space velocity of 4,000 h$^{-1}$ and vaporiser and oven temperatures of 280° C.
Fixed bed was operated for 2 hours, and the experiment had to be stopped because of severe pressure increase in the catalytic bed, due to tar like products formation.

Example 21

Acrolein Production from Glycerol

A PW/Ti dehydration catalyst was prepared as follows: 89 mg of 85% phosphoric acid (Aldrich) and 2.33 g of ammonium metatungstate (Fluka) were dissolved in 7.5 g of deionized water to obtain an aqueous solution of tungstophosphoric acid. 7.6 g of the resulting aqueous solution was then sprayed onto 15.4 g of TiO$_2$ powder obtained by grinding anatase type TiO$_2$ pellets (ST31119 from Norpro Saint Gobain) to 35 to 48 mesh. The resulting powder was dried at 110° C. for 2 hours and then was fired in nitrogen atmosphere at 500° C. for 3 hours to obtain a titania carrier supporting 10% of tungstophosphoric acid. This titania carrier was sieved to obtain a particle size of 35 to 48 mesh.

A stainless steel tube (internal diameter 13 mm) was loaded successively with 2.4 ml of CsPMo catalyst from example 1 and with 9.6 ml of PW/Ti catalyst to form a fixed catalytic bed.

An aqueous solution of glycerin (at a concentration of 50% by weight) was fed to an evaporator at a flow rate of 12.4 g/hr together with nitrogen (14.4 NL/hr) and with oxygen (0.95 NL/hr) at 280° C. so that glycerin was gasified and the resulting gasified glycerin was passed through the fixed catalytic bed, first through the PW/Ti catalyst bed then through CsPMo catalyst bed. The fixed catalytic bed was heated with an electric oven at a temperature of 280° C. Feed gas had a following composition in mol %:glycerol:oxygen:nitrogen:water=6.2:3.5:58.5:31.5. Gas Hourly Space Velocity (GHSV) of the first catalyst was 2,500 h$^{-1}$ and that of the second catalyst was 10,000 h$^{-1}$. GHSV is the ratio of the flow of feed gas (expressed in normal liter per hour) by the volume of catalyst (expressed in liter). Pressure in the reactor was 1.7 bar gauge.

In order to characterize the composition of the gas flow out the reactor, products were condensed in a condenser charged with demineralized water. Liquid aqueous phase and gaseous vents were quantitatively analyzed by gas chromatographs (HP 6890 Agilent, FFAP column, FID detector, CP4900 Varian, Silicaplot and Molecular Sieve 5 Å, TCD detectors). Proportions of products were corrected in factors from the results of the gas chromatograph to determine absolute amounts of products.

The conversion (%) of material, the selectivity of objective substance and the yield of objective substance are determined by following equations:

The conversion (%) of material=(mole number of material reacted/mole number of material supplied)×100

The selectivity (%) of objective substance=(mole number of objective substance obtained/mole number of material reacted)×100

The yield (%) of objective substance=(mole number of objective substance obtained/mole number of material fed)×100

The propanal/acrolein molar ratio (%)=(mole number of propanal obtained/mole number of acrolein obtained)×100

Results are shown in Table 4.

Example 22

Comparative

The same experiment as in example 21 was reproduced by using only one single catalyst in the catalytic bed: 9.6 ml of PW/Ti catalyst was loaded in the catalytic bed. Results are shown in Table 4.

TABLE 4

| Example | 21 | 22(comparative) |
|---|---|---|
| Glycerol conversion (%) | >99 | >99 |
| Acrolein yield (%) | 49 | 76 |
| Acrylic acid yield (%) | 25 | 0.3 |
| Propanal yield (%) | 0.02 | 0.7 |
| Propionic acid yield (%) | 0.2 | 0.13 |
| Acetic acid yield (%) | 8.6 | 0.4 |
| Acetaldehyde yield (%) | 2.3 | 1.6 |
| Hydroxypropanone yield (%) | 0 | 0.2 |
| Propanal/acrolein molar ratio (%) | 0.04 | 0.92 |

Example 23

Acrylic Acid Production from Glycerol with a Step of Selective Elimination of Propanal A simulation using the ASPEN PLUS® software was used to illustrate the method according to the invention.

In this example, % wt means % by weight and ppmwt means part per million by weight.

We mentioned only the components at a concentration above 1% wt.

A gas stream at 320° C. under 2.8 bar (82.5 t/h, 20.8% wt glycerol, 51.7% wt water, 21.8% wt carbon dioxide, 5.3% wt oxygen) is sent to a multitube fixed bed reactor containing a heterogeneous dehydration catalyst coupled with a molten salt bath.

A gas stream leaves this reactor at 320° C. under 1.8 bar (82.5 t/h, 59.8% wt water, 4.2% wt oxygen, 10.2% wt acrolein, 22.4% wt CO$_2$). This gas stream contains 650 ppmwt of propanal. This stream is cooled to 102° C. in a series of heat exchangers. A liquid phase (26.7 t/h, 97% wt water) is removed and the gas phase is sent to the lower part of condensation column, that comprises a condenser at its top to generate a liquid reflux in the column. Another gaseous flow is injected at the bottom of the column (35.9 t/h, 123° C., 76.3% wt CO$_2$, 16.5% wt water, 3.0% wt CO, 1.9% wt O$_2$). The gas phase that goes out the condenser (69.5 t/h, 74° C., 1.7 bar, 65.9% wt CO$_2$, 12.1% wt acrolein, 10.8% wt water, 6.0% wt O$_2$, 2.4% wt CO, 1.3% wt acetaldehyde, 770 ppmwt propanal) is heated to 240° C. in a heat exchanger.

This stream is sent to the top of a multitubular fixed bed reactor that comprises 2 sections. Each section is coupled with a specific molten salt bath. The upper section contains a catalyst for selective elimination of propanal and the salt bath of this section is kept at 300° C. The lower section contains a catalyst for the oxidation of acrolein to acrylic acid and the salt bath of this section is heated to 260° C.

After the first section, the gas flow contains 66.6% wt CO$_2$, 11.8% wt acrolein, 11.0% wt water, 5.4% wt O$_2$, 2.4% wt CO, 1.3% wt acetaldehyde, 120 ppmwt propanal.

At the outlet of the reactor, the gas stream contains 67.2% wt CO$_2$, 14.4% wt acrylic acid, 11.2% wt water, 1.1% wt O$_2$, 2.6% wt CO, 1.1% wt acetic acid, and 70 ppm propionic acid.

This stream is cooled to 160° C. and injected in an absorption column. At the top of this column, water (6.5 t/h) is injected. The liquid that is recovered at the bottom of the column is send to a second column that is operated under vacuum. A stream of acrylic acid is recovered at the bottom of this column (15.5 t/h, 63.6% wt acrylic acid, 27.7 wt % water, 4.9% wt acetic acid, 3.0 wt % formic acid and 300 ppmwt propionic acid).

Example 24

(Comparative): Acrylic Acid Production from Glycerol without Selective Elimination of Propanal The same simulation as in example 23 was reproduced with a second multitubular fixed bed reactor that comprises only one section. This section contains a catalyst for the oxidation of acrolein to acrylic acid and the salt bath of this section is heated to 260° C. The stream of acrylic acid that is recovered at the bottom of the last column contains 63.8% wt acrylic acid, 27.7 wt % water, 4.9% wt acetic acid, 3.0 wt % formic acid and 2000 ppmwt propionic acid.

Example 25

Methylmercaptopropionaldehyde Production from Glycerol with Selective Elimination of Propanal The same experiment as in example 21 is reproduced. The hot acrolein gases out of the reactor are quenched in cold water in order to get an aqueous phase containing around 3% wt acrolein. This aqueous phase is further distilled. Acrolein containing 96% wt acrolein, 0.4% wt acetaldehyde, 3% wt water and 0.04% wt propanal is recovered. A reaction mixture consisting of 25 g of methylmercaptopropionaldehyde and 0.85 g of a mixture of 48% wt of pyridine in acetic acid is introduced in a 250 ml reactor, At 60° C., 89.4 g of the obtained acrolein and 74.9 g of 99.5% wt methylmercaptan are simultaneously introduced in this reaction mixture over a 30 minute period and reaction is continued for 10 minutes then the mixture is cooled. Methylmercaptopropionaldehyde is obtained and can be used without further purification or with a purification by distillation under reduced pressure for methionine or 2-hydroxy-4-(methylthio)butyric acid synthesis.

What is claimed is:

1. A process for the purification of acrolein by selective removal of propanal from an acrolein-rich stream, said process comprising the step of passing said stream in gas phase in the presence of oxygen through a molybdenum-containing catalyst comprising at least molybdenum and at least one element selected from the group consisting of P, Si, W, Ti, Zr, V, Nb, Ta, Cr, Mn, Fe, Co, Ni, Cu, Zn, Ga, In, Tl, Sn, Ag, As, Ge, B, Bi, La, Ba, Sb, Te, Ce, and Pb,
   wherein the concentration of acrolein ranges from 1 to 12 mole % in the gas stream passed through the catalyst and,
   whereby said propanal is more converted than acrolein on the catalyst, said propanal is not converted to propionic acid in an amount higher than 50%, and, after purification, the amount of propanal in said acrolein-rich stream is lower than 5000 ppm.

2. Process according to claim 1 wherein the catalyst is chosen from the group consisting of molybdenum-containing mixed metal oxides and molybdenum-containing heteropolyacids.

3. Process according to claim 2 wherein the catalyst comprises iron molybdate mixed oxide.

4. Process according to claim 2 wherein the catalyst is one molybdenum-containing heteropolyacid.

5. Process according to claim 4 wherein the catalyst comprises at least one molybdenum-containing heteropolyacid in which a proton in the heteropolyacid is partially exchanged by at least one cation selected from elements belonging to Group 1 to 16 of the Periodic Table of elements.

6. Process according to claim 1 wherein the catalyst is one molybdenum-containing mixed metal oxide.

7. Process according to claim 1 wherein the catalyst is represented by the formula:

$$A_a X_b Y_c Z_d O_e$$

wherein:
   A is more than one cation selected from elements belonging to Group 1 to 16 of the Periodic Table of Elements and lanthanides
   X is P or Si
   Y is Mo
   Z is more than one element selected from the group comprising W, Ti, Zr, V, Nb, Ta, Cr, Mn, Fe, Co, Ni, Cu, Zn, Ga, In, Tl, Sn, Ag, As, Ge, B, Bi, La, Ba, Sb, Te, Ce and Pb,
   a, b, c and d satisfying following ranges:
   $0 \leq a \leq 9$,
   $0 \leq b \leq 2$
   $0 < c \leq 12$
   $0 \leq d < 12$
   and e is a number determined by the oxidation of the elements.

8. Process according to claim 1 wherein the catalyst is loaded on a support.

9. Process according to claim 1 wherein prior to purification the amount of propanal ranges from 1/4000 to 1/5 expressed by the moles of propanal relative to the moles of acrolein present in the acrolein-rich stream.

10. Process according to claim 1 wherein the acrolein-rich stream is obtained by catalytic oxidation of propylene.

11. Process according to claim 1 wherein the acrolein-rich stream is obtained by dehydration of glycerol in the presence of a catalyst containing no molybdenum.

12. Process according to claim 1 wherein purification of an acrolein-rich stream and the selective removal of propanal are carried out in a tandem-type reactor.

13. Process according to claim 1 wherein purification of an acrolein-rich stream and the selective removal of propanal are carried out in a single-type reactor.

* * * * *